United States Patent

Clayman et al.

[11] Patent Number: 5,300,080
[45] Date of Patent: Apr. 5, 1994

[54] STEREOTACTIC INSTRUMENT GUIDED PLACEMENT

[76] Inventors: David Clayman; Tai Q. Nguyen, both c/o University Medical Ctr., 655 W. 8th St., Jacksonville, Fla. 32209

[21] Appl. No.: 786,278
[22] Filed: Nov. 1, 1991
[51] Int. Cl.⁵ .............................................. A61B 5/103
[52] U.S. Cl. ..................................... 606/130; 604/117
[58] Field of Search ................. 606/130; 128/653.1, 128/898; 378/20, 205; 604/117

[56] References Cited

U.S. PATENT DOCUMENTS

| | | | |
|---|---|---|---|
| 3,053,256 | 9/1962 | Cooper et al. | 606/130 |
| 3,223,087 | 12/1965 | Vladyka et al. | |
| 3,964,480 | 6/1976 | Froning | 604/117 |
| 4,583,538 | 4/1986 | Onik et al. | |
| 4,608,977 | 9/1986 | Brown | |
| 4,617,925 | 10/1986 | Laitinen | |
| 4,618,978 | 10/1986 | Cosman | 606/130 X |
| 4,706,665 | 11/1987 | Gouda | |
| 4,892,520 | 1/1990 | Gilbaugh | 604/117 |
| 4,991,579 | 2/1991 | Allen | 606/130 X |
| 4,998,938 | 3/1991 | Ghajar et al. | 606/130 |
| 5,050,608 | 9/1991 | Watanabe | 606/130 X |
| 5,078,140 | 1/1992 | Kwoh | 606/130 X |

OTHER PUBLICATIONS

"Calculus; One and Several Variables" by Salas et al, Xerox College Publishing, 1971, pp. 486 through 529.
Kelly et al; "Evolution of Contemporary Instrumentation for . . . ", Surg Neurol, 1988; 30:204-15.
Cook brochure, "Stereotaxic Guide Percutaneous Intracranial Procedures within the CT Suite"; copyright 1990.
Jones et al, "A Low Cost Modification of an Old Leksell Stereotactic . . . ", British Journal of Neurosurgery (1990) 4, 193-198.
Couldwell et al, "Initial Experience Related to the use of the . . . " J. Neurosurg./vol. 72/Jan., 1990, pp. 145-148.
Heilbrun et al, "Brown-Roberts-Wells Stereotactic Frame Modifications . . . ", Proceedings of the Meeting of the American Society for Stereotactic Functional Neurosurgery, Montreal, 1987, Appl. Neurophysiol. 50: 143-152 (1987).
Wells et al, "The Brown-Roberts-Wells (BRW) Arc: Its Concept . . . " Proceedings of the Meeting of the American Society for Stereotactic Functional Neurosurgery, Montreal, 1997, Appl. Neurophysiol. 50: 127-132 (1987).
Cosman et al, "Combused Use of a New Target-Centered Arc System . . . " Proceedings of the Meeting of the American Society for Stereotactic and Functional Neurosurgery, Montreal 1987, Appl. Neurophysiol. 50: 119-126 (1987).
Hitchcock, "Stereotactic-Computerized Tomography Interface Device", Proceedings of the Meeting of the American Society for Stereotactic and Functional Neurosurgery, Montreal 1987, Appl. Neurophysiol. 50: 63-67 (1987).
Ebina et al, "Development and Clinical Usefulness of a New Neuroendoscope System . . . ", Neurol Med Chir (Tokyo) 30, 401-407, 1990.

*Primary Examiner*—Peter A. Aschenbrenner
*Attorney, Agent, or Firm*—Nixon & Vanderhye

[57] ABSTRACT

A stereotactic neurological instrument placement guide is utilized to facilitate ventriculostomy procedures, or other neurological procedures such as biopsy, radioactive seed placement, and lesion generation. The guide has a pair of point members disposed on a common linear axis. The proposed position of a burr hole in the patient's skull is marked, the location of a target point (e.g. ventricle) within the patient's skull is decided upon, and the patient is given a CT or MRI scan. Utilizing data from the scan, a coordinate line is calculated between the burr hole proposed position and the target point. Utilizing the calculated coordinate line, a fixing point on the patient's skull opposite the proposed position of the burr hole is determined, and the fixing point is marked. The instrument guide is placed into operative association with the patient's skull so that the opposed point members engage the burr hole and the fixing point, and then a neurological instrument is passed into the burr hole positively guided by the instrument guide until the instrument reaches the target point at which a neurological procedure is performed. Calculations establishing the coordinate line are obtained by vector parameterization, utilizing a programmable scientific calculator.

18 Claims, 3 Drawing Sheets

STEREOTACTIC INSTRUMENT GUIDED PLACEMENT

BACKGROUND AND SUMMARY OF THE INVENTION

There are many neurological procedures which require the accurate placement of a neurological instrument, including for biopsy, radioactive seed placement, and lesion generation. One of the most common neurological procedures requiring accurate placement is a ventriculostomy procedure in which a cerebral ventricle drain or shunt is installed. Such a drain or shunt is utilized for ventricular drainage when a patient manifests hydrocephalus resulting from congenital brain malformations, acute or chronic infections, tumors, intraventricular hemorrhage, or normal pressure hydrocephalus.

Conventional procedures for the placement of ventricular drains or shunts rely heavily on the skill of the neurosurgeon, and/or are relatively expensive and time consuming. After a CT scan, or other imaging, the neurosurgeon forms a burr hole in the skull, and then the neurosurgeon guides a catheter through the burr hole toward landmarks on the opposite side of the patient's head. It is necessary that the neurosurgeon be able to completely accurately visualize the internal tomography of the brain when performing this procedure, and it is presumed that the catheter is properly located when the surgeon obtains fluid returned through the catheter. In some circumstances, the neurosurgeon feels it advisable to check the location of the catheter, and for that purpose the patient must be subjected to another CT scan of the brain in order to verify proper location of the catheter. Since each separate, individual, CT scan is expensive, and since the prior art procedures are time consuming both for the neurosurgeon and the anaesthesiologist, there has long been a need for procedures more regularly and inexpensively accurately placing ventricular drain or shunt catheters, which will result in longer shunt patency and decreased morbidity due to shunt malposition.

According to one aspect of the present invention, a stereotactic neurological instrument placement guide is provided that may be utilized in numerous different types of neurological procedures, and which has ideal suitability for use in ventriculostomy procedures. The guide according to the invention is simple to construct and to utilize, and can readily enhance accuracy, reduce time, increase confidence, and reduce cost for a given level of confidence, in ventriculostomy procedures and other neurological treatment methods.

The stereotactic guide according to the invention has only first and second skull engaging point members, which have a common central axis. A frame mounts the skull engaging point members for controlled movement with respect to each other along the central axis. Means are provided defining a linear guide passage in the first point member, a straight line extension of the linear guide passage extending along a common central axis, and the linear guide passage is large enough for the passage of a neurological instrument (e.g. catheter or shunt) through it. The termination of the first point member coaxial with the linear passageway and common central axis provides for stabilizing the first point member in a burr hole; for example the termination may comprise a truncated cone.

The point members may be attached to arms, which in turn are attached to a guide sleeve and a guide element (bar or rod) which are movable with respect to each other. A locking screw can lock them in a position to which they have been moved, or they may be biased toward each other by an elastic band, spring loading, or the like. The means defining a linear passage may comprise a slotted sleeve rigidly fixed to the frame arm, with a slotted tubular element received within the sleeve and rotatable from one position in which the slots of the sleeve and tubular member are not aligned, to a second position in which the slots are aligned. When the slots are not aligned, the guide passage is closed and provides positive guiding of the catheter therethrough. When the slots are aligned, the placement guide may be removed from contact with the patient's skull, and the catheter.

According to the present invention, the key to proper utilization of the stereotactic neurological instrument placement guide is the proper location of the fixing point on the opposite side of the patient's skull from the burr hole. The positive location of the fixing point, which will receive the second point member of the placement guide, opposite the proposed site for the burr hole is determined utilizing a CT scan, magnetic resonance imaging (MRI), or another type of coordinate multiplanar tomographic imaging of the patient's skull. Utilizing X, Y, and Z coordinates for the burr hole (marked by a nipple marker or the like), and determining the coordinates of the particular portion of the ventricle, or other location within the brain, desired to be acted upon by the neurosurgeon, the data from the imaging can be used to calculate the loci of points along a straight line between the burr hole and the target area, which loci can be extended to the patient's skull on the opposite side thereof from the burr hole, and that part of the patient's skull can be marked with a nipple marker, oil, or the like. The calculations are preferably provided by vector parameterization, utilizing a programmable scientific calculator, and the gantry angle of the imaging equipment can be automatically accommodated.

Desirably the distance of the target point from the burr hole is also calculated according to the invention, so that the neurosurgeon can use indicia on the catheter to determine when the catheter has been inserted the distance necessary to properly position it at the target. Practicing the method according to the invention, since the placement of the fixing point is accurately determined, there is no necessity for a second CT scan, or the like.

While the invention will be described herein primarily with respect to ventriculostomy procedures, it is to be understood that both the apparatus and procedures according to the invention may be applied to a wide variety of neurological practices. In fact, the basic positioning facilitating features according to the invention are applicable not just to neurosurgery, but in general to determining the position of a line between two points on or within a human patient's body utilizing data normally determined from a coordinate multiplanar tomographic imaging (CT, MRI, etc.) of the patient's body during which the patient is disposed at an angle, and is incrementally advanced between images. Utilizing the present invention it is possible to practice procedures not heretofore contemplated, or to maximize the accuracy of present procedures, since according to the invention it is possible to accurately locate and determine the coordinates of two or more points on or within a human body (e.g. within the brain).

DETAILED DESCRIPTION OF THE DRAWINGS

Figure 1:
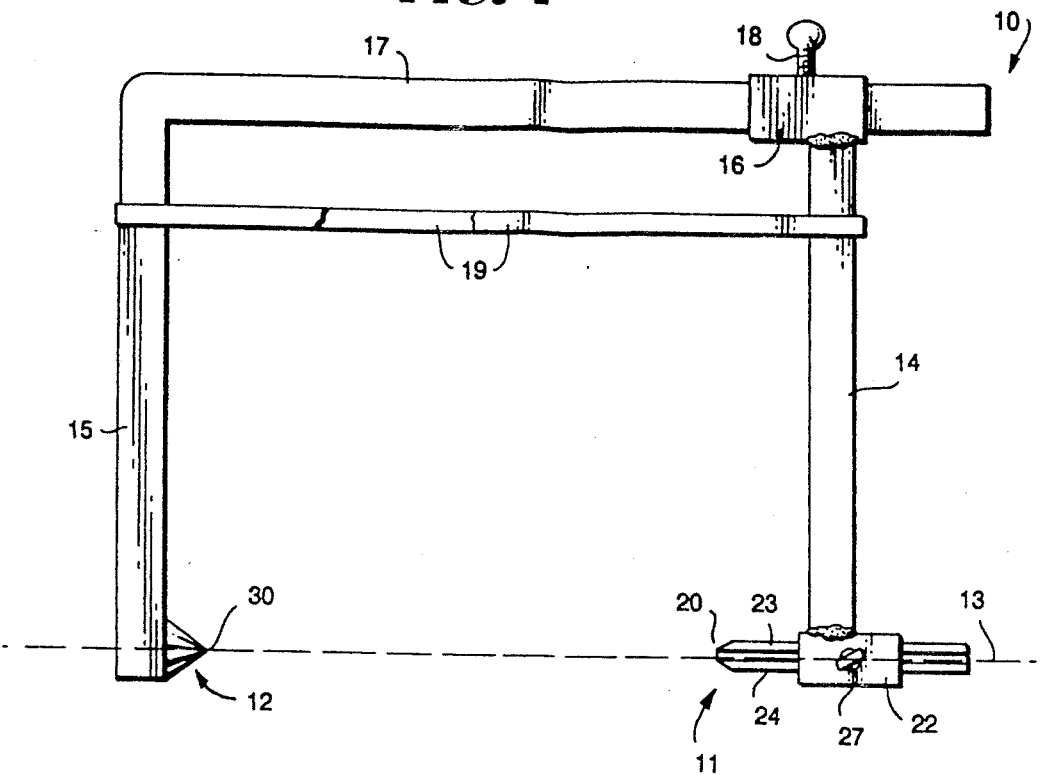
FIG. 1 is a side view of an exemplary stereotactic neurological instrument placement guide according to the invention.
Figure 5:
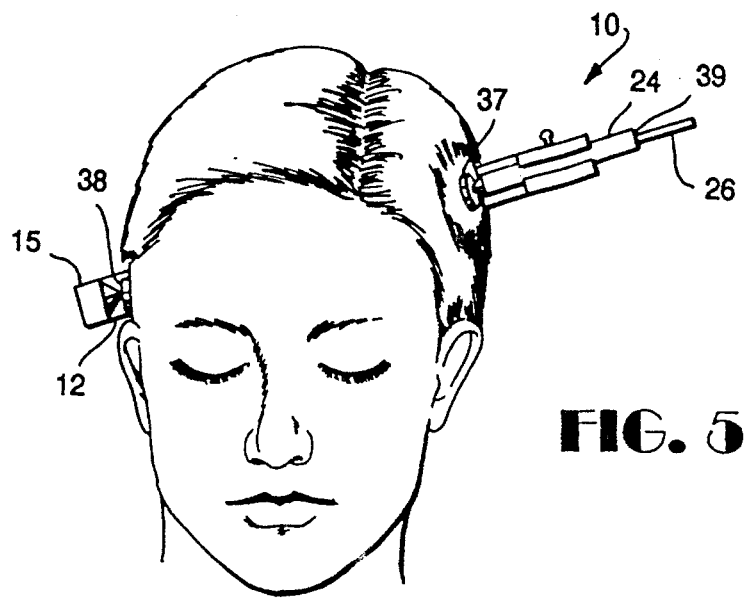
FIG. 5 is a schematic view showing the guide of FIG. 1 in use on a patient's head with a catheter having been placed by the guide.

FIGS. 1 and 5 illustrate an exemplary stereotactic neurological instrument placement guide according to the invention, shown generally at reference numeral 10. The guide 10 preferably is made of lightweight, rigid material, such as aluminum, titanium, hard plastic, or the like. It includes only two skull engaging elements, that is the skull engaging elements consist of a first skull engaging point member shown generally by reference numeral 11, and a second skull engaging point member shown generally by reference numeral 12. A frame mounts the members 11, 12 for movement toward and away from each other along a common central axis, preferably so that they move linearly with respect to each other along the linear axis 13. The frame preferably comprises a first arm 14, which preferably is rigidly connected to the first point member 11, and a second arm 15 which preferably is rigidly connected to the second point member 12. Movement of the arms 14, 15 with respect to each other, with the members 11, 12 along the axis 13, is preferably provided by a sleeve 16 rigidly attached to the first arm 14, and a guide element, such as a rod or bar, 17 rigidly connected to the second arm 15. The portions 15, 17 can be formed integrally (as by molding), as can the portions 14, 16.

In most circumstances, it is desirable to either be able to lock the frame of the device 10 so that the members 11, 12 are positioned at a specific distance from each other (corresponding to the dimension of the patient's skull at the operative area of use), or means are provided for biasing the arms 14, 15 toward each other, or for biasing the first member 11 toward the second member 12. Where locking is desired, a thumbscrew 18 may be provided threaded through an opening in the guide sleeve 16 and releasably engaging the guide element 17. When the guide element 17 is tightly engaged, relative movement between the arms 14, 15 is not possible, but when the thumbscrew 18 is loosened relative movement in a dimension parallel to the axis 13 is possible. Instead of, or in conjunction with, the thumb locking screw 18, an elastic band 19 may be provided, which exerts a force pulling the arms 14, 15 toward each other. Alternatively (not shown) a spring loading can be provided for the first point member 11 itself, the spring loading operating between the arm 14 and the end, skull engaging, termination 20 of the member 11, so that it is biased into contact with the patient's skull.

It is very desirable to be able to remove the guide 10 from contact with the patient's skull, and from contact with the neurological instrument (e.g. catheter), once the stereotactic device 10 has been utilized to properly guide the neurological instrument into place. This may be accomplished by the means most clearly illustrated in FIG. 2.

Figure 2:
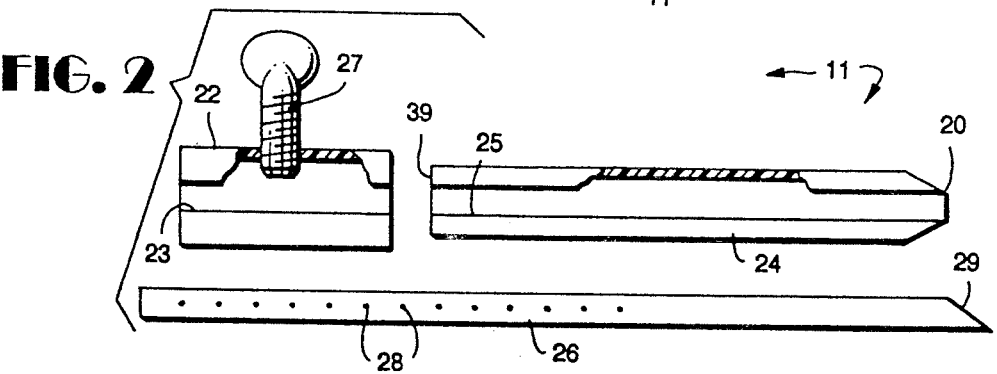
FIG. 2 is a side exploded view, partly in elevation and partly in cross-section, of the components associated with the first skull engaging point member of the guide of FIG. 1.

FIG. 2 illustrates the first point member 11 as a slotted sleeve 22 which is rigidly attached to the arm 14, with the slot 23 therein preferably on the opposite face of the sleeve 22 as the arm 14. Disposed within the sleeve 22 is the slotted tubular element 24, having a slot 25 in one face thereof along the length thereof, both the slots 23 and 25 having a width which is great enough so that a catheter 26, or other neurological instrument, may be removed therethrough. Also, the internal diameter of the tubular element 24 is such that it provides a relatively tight fit for the catheter 26, but so that the catheter can move longitudinally therethrough. If the arm 14 is made of metal, it is desirable to make the slotted sleeve of a similar metal, while it is desirable to make the tubular member 24 of nylon, or a similar relatively rigid, durable plastic with lubricity characteristics.

The position of the tubular element 24 within the slotted sleeve 22 can be fixed by tightening the thumbscrew 27 which passes through the side wall of the sleeve 22, perpendicular to the dimension of elongation of the interior passageway, and the slot 23, therein. End termination 20 of the tubular element 24 actually engages a burr hole in the skull, and is preferably shaped in a manner so as to stabilize the first point member within the burr hole. This can be accomplished, as illustrated in FIGS. 1 and 2, by forming the termination 20 as a truncated cone.

Note that the catheter 26 preferably has indicia 28 formed along the length thereof. The position of those indicia with respect to a fixed point on the device 10 (typically on the tubular element 24) can be used as a guide by the neurosurgeon for insertion of the catheter 26 to make sure that it has been inserted to the proper position, i.e. so that the lead tip 29 thereof is at the target location in the brain ventricle or other target area.

Figure 3:
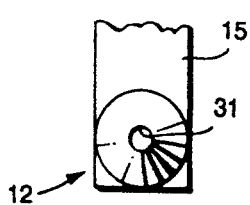
FIG. 3 is an end view of a second embodiment of the second skull engaging point member of the guide of FIG. 1.

It is preferred that the second skull engaging point member 12 merely comprise a conical element terminating in a tip 30, which is integral with or rigidly affixed to the arm 15. However, under some circumstances it may be desirable to form the termination of the second point member 12 so that it can surround a nipple marker, to facilitate accurate placement. Such a second skull engaging point member is shown generally by reference numeral 12' in FIG. 3, the member 12' being formed as a hollow truncated cone, with means defining an interior surface 31 which is circular and has a diameter approximately equal to the outside diameter of a nipple marker 32 (see FIG. 4).

Figure 4:
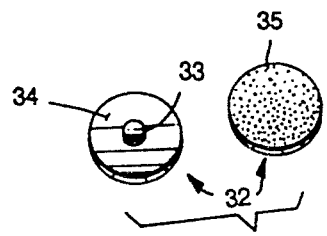
FIG. 4 illustrates a pair of nipple markers that may be utilized in the practice of the method of the invention, one shown in top perspective and the other in bottom perspective.

FIG. 4 illustrates conventional nipple markers that may be utilized with the device 10 to ensure proper positioning thereof in the surgical procedures according to the invention. The conventional nipple markers 32 are discs of plastic, or like material that is not clearly visible in a CT, MRI, or other imaging procedure, with a small cylinder of lead (or like radiopaque material) 33, having a diameter of about one-two millimeters, on the top face 34, concentric therewith. The top face 34 is smooth and uncoated, while the bottom face 35 has adhesive affixed thereto (it may have a release paper covering). In use, when a nipple marker 32 is in place, a scribe mark on the skull can be provided by passing a trocar or screw around disc 34. Alternatively, an entire nipple marker 32 may be used for placement, for example with respect to the second point member 12' of FIG. 3.

FIG. 5 illustrates utilization of the device 10 in the placement of a ventricular drain or shunt. Nipple markers 32 are placed where a burr hole 37 is to be formed in the patient's skull at a location determined to be acceptable for the particular patient and procedure involved by the neurosurgeon, and at a fixing point 38 on the opposite side of the patient's skull from the burr hole 37. The manner in which the fixing point 38 is precisely located will be described hereafter.

The neurosurgeon moves the first arm 14 so that it is widely spaced from the second arm 15, and then moves the second point member 12 into operative contact with the fixing point 38. Then the arm 14 is moved toward the arm 15, with the members 11, 12 moving along a common linear axis 13, until the termination 20 of the member 11 is stabilized within the burr hole 37. During this initial phase, the position of the arm 14 with respect to the arm 15 may be fixed, and the tubular element 24 may slide with respect to the slotted sleeve 22, or vice versa.

Once the termination 20 has properly stabilized within the burr hole 37, either the thumbscrew 18 can be tightened to lock the relative positions of the arms 14, 15 in place (with the thumbscrew 27 likewise tightened), or the elastic band 19 can be placed around the arms 14, 15 to bias them together. When the device 10 is in this position, it is necessary to be sure that the slots 23, 25 are misaligned with each other so that when the catheter 26 is passed therethrough it cannot move sidewardly out of the guide provided by the slotted sleeve 22 and tubular element 24.

With the device 10 thus so positioned, the neurosurgeon then moves the catheter 26 into the guide provided by the sleeve 22 and element 24, inserting it into the skull until the appropriate indicia 28 is reached (e.g. at the top surface 39 of the element 24) indicating that the catheter 26 has been inserted a distance calculated to be the distance of the ventricle area to be drained from the burr hole 37.

Once the catheter 26 has been thus properly positioned it is desirable to be able to remove the device 10 from operative engagement with the patient's head, and the catheter 26. This is accomplished by loosening the thumbscrew 27, then rotating the tubular member 24 so that the slot 25 therein is aligned with the slot 23 in the sleeve 22, the slots 23, 25 providing a channel which is open, and then—with the termination point 20 pulled away from the burr hole 37 (either by moving the tubular element 24, or by moving the entire arm 14)—moving the device 10 in the direction of the guide element 17 (that is away from the patient's head) so that the catheter passes through the channel defined by the slots 23, 25. Thus the catheter 26 remains in place while the device 10 is completely detached.

It is to be understood that a wide variety of modifications may be made in the stereotactic placement guide 10. For example, the tubular element 24 could be continuous, rather than slotted, and it could be removed from engagement with the catheter 26 by pulling it out over the top of the catheter 26, along the length thereof, and then the catheter 26 moved out through the slot 23. Also the sleeve 22 could be pivotally connected to the arm 14, or detachably connected thereto, and a wide variety of other modifications are also possible.

Figure 8:
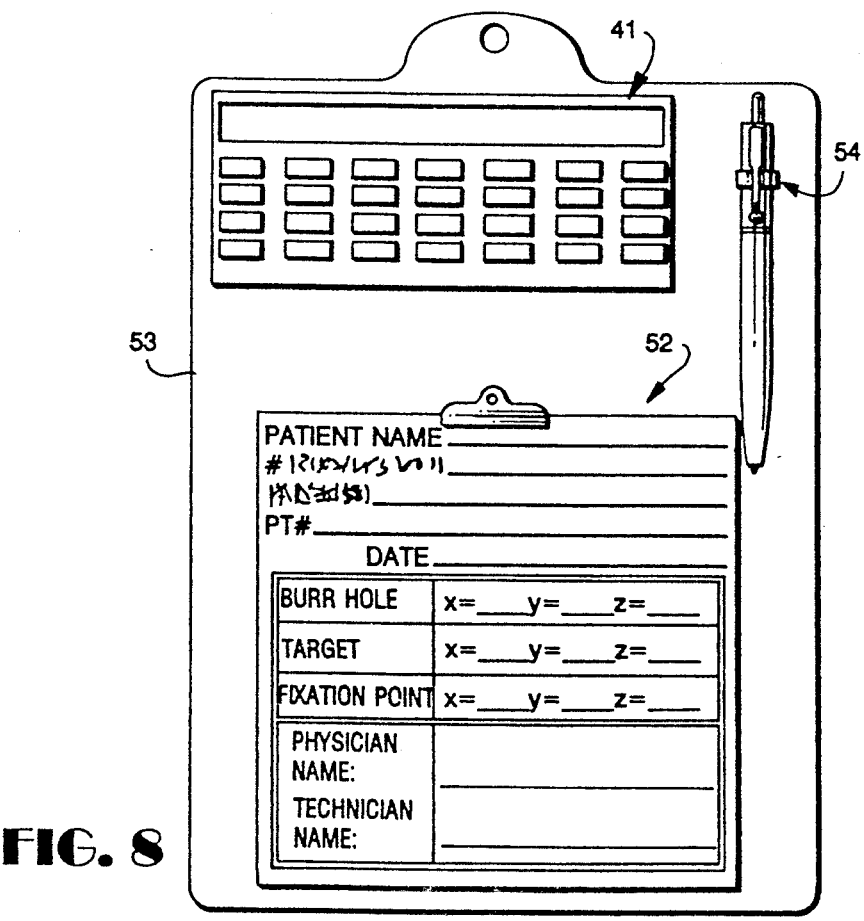
FIG. 8 is a top plan view of a programmable calculator and record keeping pad mounted in a manner facilitating its utilization in the practice of the method according to the invention.

According to the present invention, it is necessary to accurately position the fixing point 38, otherwise the goals of accurate placement of the neurological instrument (e.g. catheter 26) will not be achieved. Accurate placement of the nipple marker 32, or the like, at the fixing point 38 is accomplished utilizing conventional coordinate multiplanar tomographic imaging equipment, shown schematically generally by reference numeral 40 in FIG. 6, and by utilizing a programmable calculator 41 (see FIG. 8), or a like computer.

The coordinate multiplanar tomographic imaging equipment 40 preferably is CT or MRI equipment, but other coordinate multiplanar tomographic imaging techniques and equipment may also be utilized. Such equipment 40 typically cooperates with a table 42 on which the patient rests, and the equipment 40 is disposed at a tilt or gantry angle 43 with respect to table 42 to ensure proper imaging. A computer control 44 controls the equipment 40, and desired information is viewable on the screen 45. During the imaging operation, the table 42 is incrementally advanced in the Z dimension illustrated in FIG. 6.

Figure 6:
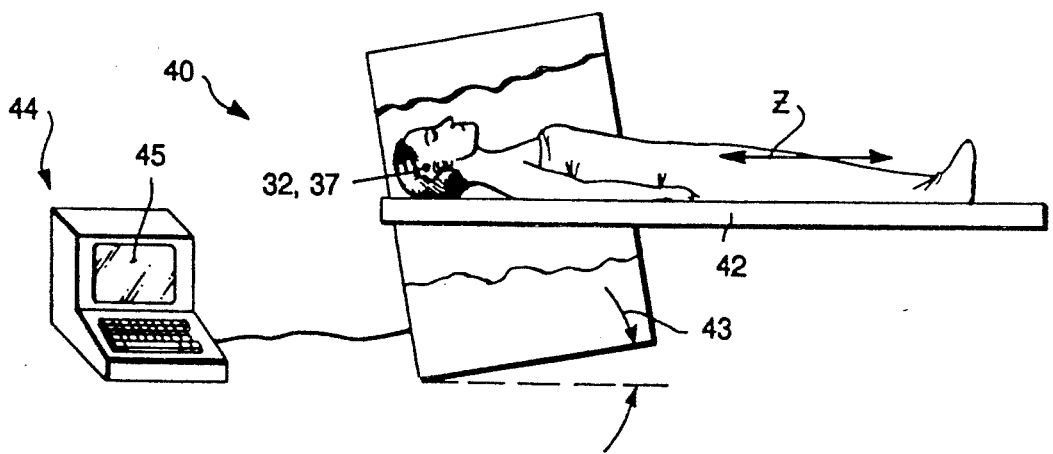
FIG. 6 is a schematic view of conventional coordinate multiplanar tomographic imaging equipment utilized in the practice of the method according to the invention.

When the patient is placed in the equipment 40, a nipple marker 32 or the like for the burr hole 37 is in place (being shown in an exaggerated size in FIG. 6). Utilizing the equipment 40, the operator determines the X, Y, and Z (Z being the position along the table 42) coordinates of that location, which is a first point. The equipment 40 operator will have already been instructed by the neurosurgeon as to what the target location in the brain has been decided upon. For example the target location may be a particular second point 47 (see FIG. 7, a representation of an image of the patient's skull on the screen 45 at one particular slice) within the ventricle 48. The coordinates of the second point 47 are also determined by the operator as is conventional.

The operator operates the equipment 40 to conduct a conventional imaging operation, e.g. CT scan. On the screen 45 all of the data associated with each slice of the imaging operation is recorded, including the position along the table 42 (the dimension Z) and the table moves an increment between each slice, the increment typically being about 5 to 10 millimeters.

Figure 7:
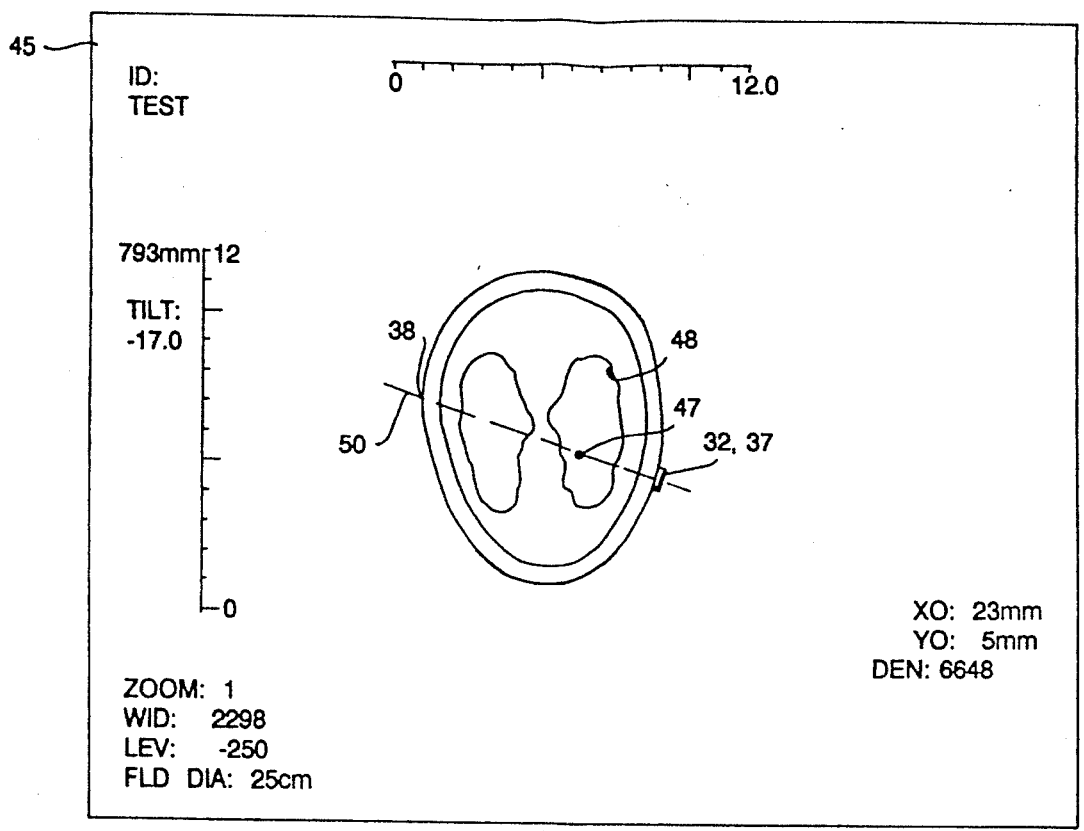
FIG. 7 is a schematic view of a screen of the apparatus of FIG. 6 at one of the slice locations.

Utilizing the coordinates of the first point 32, 37 and the second point 47 (the X, Y and Z coordinates of each), the angle of inclination 43 of the scanning equipment 40 with respect to the table 42 (the gantry angle), and the incremental advancement (the incremental advance in dimension Z, typically 5 millimeters), the distance between the first and second points can be calculated, and the loci of points along a line containing the first and second points can be determined, the line being shown schematically at 50 in FIG. 7. This calculation is performed utilizing the programmable calculator 41 or like computer, utilizing vector parameterization. FIG. 7 illustrates the points 32, 47, 38 all on the same screen only for the purposes of facilitating the description of the invention. However, in a real life use no single screen ("slice") will contain all three points since they are not coplanar with the "slices".

Pursuant to vector parameterization, as is well known per se in vector mathematics, for any line passing through a volume a vector parameterization for the line can be derived utilizing the equation $r(t)=a+tb$ where t is real and r, a and b are nonzero vectors. Vector "a" passes from the origin of the coordinate system to a point on the line to be described. Vector b is on the line and gives the line direction. t is a scalar which ranges over the set of real numbers. Varying t varies the vector r(t), but the tip of r(t) remains on the line described. Given any two points in the cartesian coordinate system, a line through these two points can be described using the vector parameterization. The line can then be extended through space by changing the scalar value t.

A representation of the various program steps that will performed by the calculator 41 in calculating the desired data is provided by the following BASIC computer program:

```
10 INPUT "BURR HOLE TABLE POSITION", C
20 INPUT "BURR HOLE X VALUE", A
30 INPUT "BURR HOLE Y VALUE", B
40 INPUT "TARGET CT TABLE POSITION", Z
50 INPUT "TARGET X VALUE", X
60 INPUT "TARGET Y VALUE", Y
70 INPUT "CT TABLE INCREMENT", M
80 INPUT "CT GANTRY ANGLE (DEGREES)", L
90 N=M*COS(L)
100 E=C*SIN(L)+B
110 F=C*COS(L)
120 V=Z*SIN(L)+Y
130 W=Z*COS(L)
140 D=CINT( (X−A)²+(V−E)²+(W−F)²)½
150 PRINT "BURR HOLE TO TARGET DISTANCE"
160 PRINT D; "MM"
170 P=W−(10*N)
180 FOR H=1 TO 20
190 K=(P−F)/(W−F)
200 Q=CINT (A+(X−A)*K)
210 R=E+(V−E)*K
220 S=F+(W−F)*K
230 U=CINT(S/COS(L))
240 T=CINT(R−U*SIN(L))
250 PRINT "TABLE POSITION=";U;",";"X=";Q;",";"Y=";T
260 P=P+N
270 NEXT H
280 STOP
```

Line 10 is the input for the burr hole Z coordinate, line 20 for the burr hole X coordinate, and line 30 for the burr hole Y coordinate. Line 40 is for the target (second point 47) Z coordinate, line 50 for the target X coordinate, and line 60 for the target Y coordinate. The calculation in line 90 thus converts the CT table increments in the original coordinate system to Z-axis movement increments in a new coordinate system. Calculation 100 converts the burr hole Y value to the new coordinate system, and line 20 converts the burr hole Z value. Calculation 120 converts the Y value of the target to the new coordinate system, and calculation 130 the Z target value. Calculation 140 is the distance of the burr hole (37) to the target (47), with the function "CINT" being a round off function ("cut integer"), which is preferably employed. This distance is printed out at 150.

Calculation 170 is the calculation of the Z value 10 incremental movements from the target Z value in the new coordinate system. The instruction on line 180 initiates the loop in the computer program. Calculation 190 determines the conversion factor for a point on a vector in three D space, calculation 200 determines the new X value for a parallel plane −10+0+10 incremental movements from the plane containing the target point (47). Calculation 210 is the new Y value for the above-mentioned parallel plane, while 220 is the calculation for the new Z value for the above-mentioned parallel plane. In calculation 230 the new Y value is converted to the original coordinate system, while calculation 240 converts the new Z value to the original coordinate system. Calculation 260 determines the new parallel plane Z value one incremental movement in the new coordinate system. Line 270 is the closing loop statement, and after H 1 to 20 has been run, 280 provides the end of program.

In the original coordinate system. An exemplary printout provided once all of the H values have been run (step 250 is completed for H 1 to 20), and the CT scan is complete, is as follows (this provides the loci of points on the calculated coordinate line):

```
71 MM
TABLE POSITION = 150 ,X =  50 ,Y =  45
TABLE POSITION = 145 ,X =  48 ,Y =  43
TABLE POSITION = 140 ,X =  45 ,Y =  40
TABLE POSITION = 135 ,X =  43 ,Y =  38
TABLE POSITION = 130 ,X =  40 ,Y =  35
TABLE POSITION = 125 ,X =  37 ,Y =  32
TABLE POSITION = 120 ,X =  35 ,Y =  30
TABLE POSITION = 115 ,X =  33 ,Y =  27
TABLE POSITION = 110 ,X =  30 ,Y =  25
TABLE POSITION = 105 ,X =  27 ,Y =  22
TABLE POSITION = 100 ,X =  25 ,Y =  20
TABLE POSITION =  95 ,X =  22 ,Y =  17
TABLE POSITION =  90 ,X =  20 ,Y =  15
TABLE POSITION =  85 ,X =  17 ,Y =  12
TABLE POSITION =  80 ,X =  15 ,Y =  10
TABLE POSITION =  75 ,X =  12 ,Y =   7
TABLE POSITION =  70 ,X =  10 ,Y =   5
TABLE POSITION =  65 ,X =   7 ,Y =   2
TABLE POSITION =  60 ,X =   5 ,Y =   0
TABLE POSITION =  55 ,X =   2 ,Y =  −3
Break in 280
Ok
```

The printout provided above may be accomplished utilizing a stand alone printer connected to the calculator 41, or by a printer associated with the calculator 41.

Utilizing the printout of table positions as provided above, the operator of the equipment 40, 41, can determine the most likely position for the third point 38. Then, with the patient still in the scanner (not having been removed from the equipment 40), the operator can return the table 42 to the desired position, train on a laser light which shows a line on the skull, then put on a nipple marker 32 at fixing point 38, and repeat the slice at that table position. Only if the new slice indicates misalignment of the fixing point 38 need the nipple marker 32 be repositioned.

The data obtained from running the equipment 40, 41 for a particular patient is preferably recorded, such as by utilizing the pad 52 mounted on the board 53 with the programmable calculator 41, to keep with the patient's file. A writing implement 54 may also be mounted on the board 53, providing an effective tool for facilitating the procedures according to the invention.

While the exemplary methods according to the invention have been described above with particular reference to a ventriculostomy procedure for a human patient, it is to be understood that the procedures are applicable to other neurological methods, such as biopsy, radioactive seed placement, and lesion generation. In general, according to the present invention a neurological instrument placement procedure for a human patient, utilizing an instrument guide having opposed point members disposed on a common linear axis, is provided, comprising the steps of substantially sequentially: (a) Marking the proposed position of a burr hole on the patient's skull. (b) Deciding upon the location of a target point within the patient's skull. (c) Effecting coordinate multiplanar tomographic imaging (e.g. CT, MRI, etc.) of the patient's skull and brain. (d) Utilizing data from step (c), calculating a coordinate line between the burr hole proposed position and the target point. (e) Utilizing the calculated coordinate line, determining a fixing point on the patient's skull opposite the proposed position of the burr hole, and marking that fixing point on the patient's skull. (f) Forming a burr hole in the patient's skull at the marked proposed burr hole position. (g) Placing the instrument guide into operative association with the patient's skull so that the opposed point members engage the burr hole and the fixing point. (h) Passing a neurological instrument into the burr hole, positively guided by the instrument guide, along the common linear axis of the opposed point members, until the instrument reaches the target point. And, (i) performing a neurological procedure with the neurological instrument at the target point.

The vector parameterization described above, according to the invention, is applicable to other medical procedures besides neurological procedures. The vector parameterization according to the invention is utilizable in general for determining the position of a line (typically a straight line) between two points on or within a human patient's body utilizing data normally determined from a coordinate multiplanar tomographic imaging of the patient's body during which the patient is disposed at an angle and while there is incremental advancement between images. Such a method comprises the following steps: (a) During coordinate multiplanar tomographic imaging of the patient's body, determining the coordinates of a first point on or within the patient's body. (b) During coordinate multiplanar tomographic imaging of the patient's body, determining the coordinates of a second point on or within the patient's body. (c) Determining the angle of inclination of the patient and the incremental advancement between images. And, (d) utilizing the coordinates of the first and second points, the angle of inclination, and the incremental advancement, by vector parameterization calculating the distance between the first and the second points and the loci of points along a line containing the first and second points.

It is to be understood that the apparatus and procedures according to the present invention are to be interpreted broadly in conformance with the following claims, so as to encompass all equivalent procedures and devices.

What is claimed is:

1. A ventriculostomy procedure for a human patient, utilizing a catheter guide having opposed point members disposed on a common linear axis, comprising the steps of substantially sequentially:
    (a) marking the proposed position of a burr hole on the patient's skull;
    (b) deciding upon the location of a ventricle, desired to be drained, within the patient's skull, to define an intraventricular target point;
    (c) effecting coordinate multiplanar tomographic imaging of the patient's skull and brain;
    (d) utilizing data from step (c), calculating a coordinate line between said burr hole proposed position and said intraventricular target point;
    (e) utilizing the calculated coordinate line, determining a fixing point on the patient's skull opposite the proposed position of the burr hole, and marking that fixing point on the patient's skull;
    (f) forming a burr hole in the patient's skull at the marked proposed burr hole position;
    (g) placing the catheter guide into operative association with the patient's skull so that the opposed point members engage the burr hole and the fixing point;
    (h) passing a catheter into the burr hole, positively guided by the catheter guide, along the common linear axis of the opposed point members, until the catheter tip reaches the intraventricular target point; and
    (i) draining fluid from the area of the patient's brain around the intraventricular target point.

2. A procedure as recited in claim 1 comprising the further step, between steps (h) and (i), of removing the catheter guide from contact with the patient or the catheter.

3. A procedure as recited in claim 1 wherein step (d) is practiced by vector parameterization.

4. A procedure as recited in claim 1 wherein the catheter has indicia along the length thereof, and the catheter guide has a fixed point adjacent the catheter; and wherein step (d) is also practiced by calculating the linear distance along the coordinate line from the burr hole to the intraventricular target; and wherein step (h) is further practiced by passing the catheter into the burr hole the calculated distance, as determined by indicia on the catheter aligning with a fixed point of the catheter guide.

5. A procedure as recited in claim 1 wherein step (c) is practiced by CT scanning.

6. A procedure as recited in claim 1 wherein steps (a) and (e) are practiced by marking with nipple markers.

7. A neurological instrument placement procedure for a human patient, utilizing an instrument guide having opposed point members disposed on a common linear axis, comprising the steps of substantially sequentially:
    (a) marking the proposed position of a burr hole on the patient's skull;
    (b) deciding upon the location of a target point within the patient's skull;
    (c) effecting coordinate multiplanar tomographic imaging of the patient's skull and brain;
    (d) utilizing data from step (c), calculating a coordinate line between the burr hole proposed position and the target point;
    (e) utilizing the calculated coordinate line, determining a fixing point on the patient's skull opposite the proposed position of the burr hole, and marking that fixing point on the patient's skull;

(f) forming a burr hole in the patient's skull at the marked proposed burr hole position;

(g) placing the instrument guide into operative association with the patient's skull so that the opposed point members engage the burr hole and the fixing point;

(h) passing a neurological instrument into the burr hole, positively guided by the instrument guide, along the common linear axis of the opposed point members, until the instrument reaches the target point; and (i) performing a neurological procedure with the neurological instrument at the target point.

8. A procedure as recited in claim 7 wherein step (i) is selected from the group consisting essentially of biopsy, radioactive seed placement, lesion generation, and ventricle draining.

9. A procedure as recited in claim 7 wherein step (d) is also practiced by calculating the linear distance along the coordinate line from the burr hole to the target point.

10. A method of determining the position of a line between two points on or within a human patient's body, utilizing data normally determined from a coordinate multiplanar tomographic imaging of the patient's body during which there is a non-zero angle of inclination between imaging equipment and the patient and while there is an incremental advance between images, comprising the steps of:

(a) during coordinate multiplanar tomographic imaging of the patient's body, determining the coordinates of a first point on or within the patient's body;

(b) during coordinate multiplanar tomographic imaging of the patient's body, determining the coordinates of a second point on or within the patient's body;

(c) determining the non-zero angle of inclination of the imaging equipment with respect to the patient and the incremental advance between images; and (d) utilizing the coordinates of the first and second points, the non-zero angle of inclination, and the incremental advance, by vector parameterization calculating the distance between the first and the second points and the loci of points along a line containing the first and second points.

11. A method as recited in claim 10 wherein step (d) is practiced by calculating the straight line distance between the first and second points and the loci of points along a straight line containing those points.

12. A method as recited in claim 10 wherein steps (a) and (b) are practiced by CT scanning.

13. A method as recited in claim 10 wherein the first point coordinates are A, B, and C, and the second point coordinates corresponding to the first point coordinates are X, Y, and Z, and the incremental advance is M, and the non-zero angle (in degrees) is L; and wherein step (d) is practiced by calculating with a computer the following formulas:

$N = M * \cos(L)$
$E = C * \sin(L) + B$
$F = C * \cos(L)$
$V = Z * \sin(L) + Y$
$W = Z * \cos(L)$
$D = $ square root of $((X-A)^2 + (V-E)^2 + (W-F)^2)$
$P = W - (10 * N)$
$K = (P-F)/(W-F)$
$Q = A + (X-A) * K$
$R = E + (V-E) * K$
$S = F + (W-F) * K$
$U = S/\cos(L)$, and
$T = R - U * \sin(L)$, with the calculations for P, K, Q, R, S, U, and T being performed for a plurality of different positions of the patient's body during incremental advancement.

14. A method as recited in claim 13 wherein step (d) is further practiced by taking the values of S, U, and T for each of the different positions of the patient's body defining the loci of points, and from those positions selecting the position which most likely is the position of a desired third point; and then (e) repeating the coordinate multiplanar tomographic imaging of the patient's body at the supposed position for the third point to confirm that it is the desired position for the third point.

15. A method as recited in claim 14 wherein the third point is a position on the surface of the patient's body, and comprising the further step (f) of physically marking the third point.

16. A method as recited in claim 15 practiced by further using a neurological instrument guide, and wherein the first point is a proposed position for a burr hole in the patient's skull, and the second point is the location of a target within the patient's brain, and the third point is the location of a point on the patient's skull on a straight line through the patient's skull from the burr hole; and comprising the further steps of:

(g) forming a burr hole at the first point;

(h) locating the neurological instrument guide so that it engages the first and third points; and (i) using the neurological instrument guide, effecting guided passage of a neurological instrument into the patient's skull to the second point to perform a neurological procedure thereat.

17. A method as recited in claim 16 further utilizing a catheter as the neurological instrument, and wherein the second, target, point is a ventricle of the patient's brain; and wherein step (i) is practiced to pass the catheter into the ventricle, and drain the ventricle.

18. A method as recited in claim 17 comprising the further steps of maintaining the catheter in association with the patient so that it extends into the ventricle, and removing the neurological instrument guide from contact with the patient's skull and the catheter.

* * * * *